United States Patent
Burdick et al.

(10) Patent No.: US 9,694,081 B2
(45) Date of Patent: Jul. 4, 2017

(54) PROTEASE TRIGGERED RELEASE OF MOLECULES FROM HYDROGELS

(75) Inventors: Jason Alan Burdick, Philadelphia, PA (US); Robert C. Gorman, Lower Gwynedd, PA (US); Joseph H. Gorman, III, Lower Gwynedd, PA (US); Brendan Patrick Purcell, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 233 days.

(21) Appl. No.: 13/805,501

(22) PCT Filed: Jun. 17, 2011

(86) PCT No.: PCT/US2011/040811
§ 371 (c)(1),
(2), (4) Date: Mar. 6, 2013

(87) PCT Pub. No.: WO2011/163069
PCT Pub. Date: Dec. 29, 2011

(65) Prior Publication Data
US 2014/0148395 A1 May 29, 2014

Related U.S. Application Data (60) Provisional application No. 61/356,800, filed on Jun. 21, 2010.

(51) Int. Cl.
| | |
|---|---|
| A61K 38/00 | (2006.01) |
| C07K 7/00 | (2006.01) |
| A61K 47/42 | (2017.01) |
| A61K 9/06 | (2006.01) |
| A61K 38/10 | (2006.01) |
| A61K 38/18 | (2006.01) |
| A61K 38/57 | (2006.01) |
| A61K 47/24 | (2006.01) |

(52) U.S. Cl.
CPC .............. *A61K 47/42* (2013.01); *A61K 9/06* (2013.01); *A61K 38/10* (2013.01); *A61K 38/1866* (2013.01); *A61K 38/57* (2013.01); *A61K 47/24* (2013.01)

(58) Field of Classification Search
None
See application file for complete search history.

(56) References Cited

U.S. PATENT DOCUMENTS

| | | |
|---|---|---|
| 6,287,860 B1 | 9/2001 | Monia et al. |
| 2002/0055158 A1* | 5/2002 | Greene et al. ................ 435/184 |
| 2007/0259030 A1* | 11/2007 | Drapeau ...................... 424/450 |

OTHER PUBLICATIONS

Zisch et. al. Cell-Demanded release of VEGF from Synthetic biointeractive cell ingrowth matrices for vascularized tissue growth, The FASEB Journal, vol. 17, Dec. 2003 p. 2260-2263.*
Zisch et al. Cell-demanded release of VEGF from synthetic, biointeractive coil ingrowth matrices for vascularized tissue growth. FASEB J 2003, 17(15):2260-2262.*
Rodriguez et. al., Biochimica et Biophysica Acta 1803 (2010) 39-54.*
Piecha et. al., Inflamm. Res. (2010) 59:379-389.*
Verma, Bioorganic & Medicinal Chemistry 15 (2007) 2223-2268.*
Turk, 2001 Nature Publishing Group http://biotech.nature.com, Jul. 2001, vol. 19 Nature Biotechnology.*
Creemers et al. Circulation Research, Aug. 3, 2001, vol. 89, Issue 3.*
Schocken DD et al., "Prevalence and mortality rate of congestive heart failure in the United States", J Am Coll Cardiol. Aug. 1992, 20(2), 301-306.
Wilson, E.M. et al., "Region-and type-specific induction of matrix metalloproteinases in post-myocardial Infarction Remodeling", Circulation, Jun. 2003, 107, 2857-2863. Epub May 27, 2003.
Burdick, J. et al., "Sequential crosslinking to control cellular spreading in 3-dimensional hydrogels" Soft Matter, Feb. 2009, 5, 1601-1606.
Zisch et al., "Cell-demanded release of VEGF from synthetic, biointeractive cell ingrowth matrices for vascularized tissue growth", FASEB J, Dec. 2003, 17(15), 2260-2262.
Patterson, et al., "Enhanced Proteolytic Degradation of Molecularly Engineered PEG Hydrogels in Response to MMP-1 and MMP-2", Biomaterials, 31, 2010, 7836-7845.

* cited by examiner

*Primary Examiner* — Jeanette Lieb
(74) *Attorney, Agent, or Firm* — Baker & Hostetler LLP (57) ABSTRACT

The invention relates to compositions comprising (i) biocompatible hydrogel and (ii) one or more therapeutic agents contained within said hydrogel; wherein the hydrogel is cross-linked utilizing a cross-linker comprising a peptide sequence that is capable of being degraded by an enzyme; the therapeutic agent being effective as a treatment of a condition related to the presence of the enzyme.

19 Claims, 9 Drawing Sheets

Synthesis 1: HA-Aldehyde Synthesis

Synthesis 2: HA-Hydrazide Synthesis

Gel formation through mixing of Synthesis 1 and Synthesis 2:
Hydrazone formation via Hydrazide-Aldehyde reaction Gelation time 8-9 min Gelation time 2-3 min Gelation/properties controlled by HA modification and ratio of HA-Aldehyde to HA-Hydrazide

Figure 6

MMP-specific gel

Peptide crosslinker that responds to MMP-1, MMP-2

PROTEASE TRIGGERED RELEASE OF MOLECULES FROM HYDROGELS

CROSS-REFERENCE TO RELATED APPLICATIONS

This application is the National Stage of International Application No. PCT/US2011/040811, filed Jun. 17, 2011, which claims the benefit of U.S. Provisional Application No. 61/356,800 filed Jun. 21, 2010, the disclosures of which are incorporated herein by reference in their entireties.

GOVERNMENT RIGHTS

This invention was made with government support under Contract No. Grant/Contract No. R01 HL111090 awarded by the National Institutes of Health (NIH). The Government has certain rights in the herein disclosed subject matter.

TECHNICAL FIELD

The present invention concerns the use of hydrogels to locally deliver pharmaceuticals/factors based on elevated local enzyme levels.

BACKGROUND

Cardiac problems are a major global health concern. According to the American Heart Association, 1.26 million people suffer from heart attacks annually. If the patient survives, they are at a high risk for developing heart failure. Left ventricular remodeling contributes to heart failure, which in 1995, affected 2 million people (Schocken et al, J Am Coll Cardiol. 1992 August; 20(2):301-6). The incidence and death by heart failure has been steadily increasing for years, suggesting that the potential patient population may continue to grow significantly over time. Many therapeutic approaches, both pharmacologic and surgical, have been developed to treat heart failure. Most therapies are directed at patients who have already developed symptoms. Few if any are directed at patients in the early post myocardial infarction time period before symptoms develop. None are directed at limiting extracellular matrix destruction by matrix metalloproteinases. Typically, a patient suffering a heart attack is given a cocktail of medicines that can be difficult to titrate and manage. Efficacy is often not achieved. The population of heart failure patients continues to grow in spite of the current therapeutic armamentarium.

In a paper published in Circulation (June 2003, p 2857), Wilson et at determined that certain matrix metalloproteinases (MMP), such as MMP-13 are upregulated post-MI, perhaps resulting in the left ventricular remodeling that adversely affects heart function. Further, they found that the antagonist to MMP-13, TIMP, is down-regulated. In particular, this study demonstrated increased levels of MMP-13 and MT1-MMP after MI, which may have particular significance with respect to pathological remodeling. Specifically, MMP-13 is increased in end-stage cardiomyopathies and aggressive breast carcinomas. MMP-13 degrades fibrillar collagens and therefore may contribute to myocardial extracellular remodeling. Increased MT1-MMP levels within the transition and MI regions may have particular significance, for two reasons. First, MT1-MMP degrades a wide range of extracellular matrix proteins. Second, MT1-MMP can proteolytically process soluble pro-MMPs, such as pro-MMP-13,2 and thereby amplify local proteolytic activity. The LV regions in which this local induction of MT1-MMP and MMP-13 occurred were paralleled by decreased TIMP levels. The present study demonstrated that increased MT1-MMP levels and decreased TIMP-4 levels were correlated to the extent of regional LV remodeling. This regional imbalance between these specific MMPs and TIMPs probably contributed to continued regional expansion in the post-MI myocardium.

There is a need in the art for treatments to minimize left ventricular remodeling associated with MI. In addition to LV remodeling uses, there is also a need in the art to provide regional delivery of MMP inhibiting therapy that would be active only where MMP's are active.

SUMMARY

In some aspects, the invention concerns compositions comprising a biocompatible hydrogel; and a therapeutic agent contained within the hydrogel. The hydrogel is cross-linked utilizing a cross-linker comprising a peptide sequence that is capable of being degraded by an enzyme; said therapeutic agent being effective as a treatment of a condition related to the presence of said enzyme. In some embodiments, the therapeutic agent is a tissue inhibitor of matrix metalloprotease, a growth factor, or a cell homing factor. In certain embodiments, such therapeutics include tissue inhibitor of matrix metalloprotease contained within the hydrogel and the hydrogel is cross-linked utilizing a cross-linker comprising a peptide sequence that is capable of being degraded by a matrix metalloprotease; the matrix protease being inhibited by said tissue inhibitor of matrix metalloprotease.

In some compositions, the hydrogel comprises one or more of hyaluronic acid and polyethylene glycols.

Certain compositions have the peptide sequence incorporated into the cross-linker via reaction of thiol groups of cysteines with acrylates or methacrylates. Some compositions have a cross-linker that comprises the peptide sequence and at least one of hyaluronic acid or polyethylene glycol. Some compositions consist of reaction of an aldehyde-containing molecule with a hydrazide group on the end of the peptide.

In some embodiments, the tissue inhibitor of matrix metalloprotease is TIMP-3. In certain embodiments, the matrix metalloprotease is MMP-13 or MMP-2.

Another aspect of the invention concerns methods for treating myocardial infarction comprising administering to a patient in need of such treatment a composition disclosed herein. In some embodiments, the patient is a mammal. In some preferred embodiments, the patient is a human.

Yet another aspect of the invention concerns methods of delivery of an inhibitor of matrix metalloprotease comprising: (i) administering a hydrogel of disclosed herein to a patient; (ii) allowing the hydrogel to contact matrix metalloprotease; and (iii) the contact resulting in the release of at least a portion of said tissue inhibitor of matrix metalloprotease. In some embodiments, the delivery is accomplished through a syringe or catheter.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

Hydrogels containing degradable cross-linkers can be utilized in the delivery of therapeutic and/or diagnostic agents to a specified site within a patient. In the present invention, the cross-linkers comprise a peptide sequence that is degradable by particular enzymes. When one utilizes a hydrogel containing a therapeutic agent to a condition that is associated with the presence of a particular enzyme, one can selectively deliver the agent to a specified target within the patient because the enzyme will cause degradation of the cross-links which will result in release of the agent.

Any peptide sequence containing linking group that is capable of being degraded by the desired enzyme can be utilized. In some embodiments, the peptide is at least two units in length. While the peptide has no maximum length so long as it is degradable by the desired enzyme, in certain embodiments, the peptide is up to 20, 30, 50 or 100 units in length. Some peptides are at least 5 or 10 units in length. Each of these upper and lower limits are intended to be combinable to reflect some preferred peptide lengths. Examples of suitable peptides include GCRDGPQGI-WGQDRCG, GGPQGIWGQGCG, and GCGQG-WIGQPGGG.

One application concerns treatment of myocardial infarction (MI). Left ventricular (LV) remodeling after myocardial infarction, for example, is a common structural event and contributes to increased morbidity and mortality. Matrix metalloproteases (MMPs) have been demonstrated to contribute to LV remodeling after MI by contributing to the breakdown of interstinal matrix proteins like collagen and elastin. We have demonstrated that upregulation of MMPs and down regulation of their naturally occurring inhibitors, tissue inhibitors of matrix metalloproteinases (TIMPs), occur in a type, region and temporal specific manner within the myocardium after MI. The use of a broad spectrum, systemically delivered MMP inhibitor is associated with significant adverse reactions. The ability to inhibit specific MMPs in specific regions of the heart at specific times after MI will lead to improved outcomes after MI for a large number of patients.

Regional delivery of MMP inhibiting therapy that would be active only where MMP's are active can also be utilized in treatments of other conditions. Arthritis is an example of another disease where this approach could be useful. Any disease state where localized release of therapeutics where certain MMPs exist may be treated by the hydrogel systems of the invention.

One concept that is disclosed herein is the use of synthetic hydrogels that incorporate peptide sequences that degrade in the presence of certain enzyme/proteases. The degradation or breaking of these crosslinks in the hydrogel alters the crosslinking density, which in turn alters the material properties (i.e. mechanics), which alters the diffusion of molecules through the hydrogel and hence delivery into the affected tissue. One area where this approach would be important is in disease processes where there are region specific changes in the levels of MMPs. An important example of such a pathologic phenomenon is post-MI LV remodeling. There may be target molecules (e.g., TIMPs) that can alter MMP activity and treat or prevent this disease. With a material such as this, the release of these molecules will be locally dependent on the level of protease activity at those sites. For example MMP-13 is known to be upregulated in the peri-infarct region in the first 8 weeks after MI and TIMP-3 (an inhibitor of MMP-13) down regulated during this time period; a hydrogel that is degraded only in the presence of MMP-13 and released TIMP-3 locally as it was degraded would likely have a beneficial effect on LV remodeling.

Hydrogels are well known in the art and are generally formed by the reaction of a macromer having a biocompatible backbone with a cross-linking agent. Any suitable hydrogel may be utilized. Types of materials that could be used for this purpose include crosslinked synthetic hydrogels that are based on molecules like hyaluronic acid or polyethylene glycols. Suitable hydrogels also include those constructed using polyesters, polyurethanes, polysaccharides, proteins, and combinations thereof. Polyesters, poly (ethylene oxide) (PEO), proteins and the like are also suitable polymeric materials can also be used as a polymeric component of the hydrogel. General synthetic methods for making hydrogels can be found, for example in Burdick, et al, Soft Matter, 2009, 5, 1601-1606.

A partial listing of polysaccharides that are useful in the claimed invention includes hyaluronic acid, amylase, amylopectin, glycogen, cellulose, heparin, agarose, alginate, and the like. In some embodiments, hyaluronic acid or any combination thereof is particularly suitable for use in the instant invention. In some embodiments—such as those embodiments that include hyaluronic acid—the biocompatible backbone unit is capable of enzymatic degradation.

In other embodiments, the biocompatible backbone is capable of hydrolytic degradation. Those embodiments are considered useful where a user may desire a degradable macromer whose degradation is dependent primarily on exposure to aqueous medium without the additional complication of a macromer that is also susceptible to enzymatic degradation. In some embodiments, the macromer is capable of both enzymatic and hydrolytic degradation.

The macromers may include a range of polymerizing moietes, such as acrylates, methacrylates, and the like. In some embodiments, the polymerizing moiety includes a carbon-carbon double or triple bond. The moiety is suitably polymerized by photopolymerization, by free radical-initiation, or by other methods of polymerization known to those of skill in the art.

The peptide moieties can be incorporated into the cross-linkers by reaction of active hydrogen atoms. In some embodiments, the active hydrogen atoms can be part of hydroxy, thiol, or amine groups (including hydrazine). In some embodiments, the peptide can be incorporated as crosslinks through the addition reaction of thiols in cysteines in the peptides with acrylate or methacrylates, vinyl sulfones, or maleimides on these molecules.

Any useful therapeutic agent can be utilized with the present invention. In some embodiments, growth factors (vascular endothelial growth factor (VEGF), for example), stem cell homing factors (SDF-1a, for example), or tissue inhibitor of matrix metalloprotease (TIMP-1, TIMP-2, TIMP-3, and TIMP-4, for example).

In some embodiments, the therapeutic molecule may be directly encapsulated during the gelation process by mixing the molecule with the pre-cursor solutions.

The compositions of the instant invention may be administered by methods well known to those skilled in the art. Such methods include local or systemic administration. In some embodiments, administration is topical. Such methods include ophthalmic administration and delivery to mucous membranes (including vaginal and rectal delivery), pulmonary (including inhalation of powders or aerosols; intratracheal, intranasal, epidermal and transdermal), oral or parenteral. Parenteral administration includes intravenous, intraarterial, subcutaneous, intraperitoneal or intramuscular injection or infusion; or intracranial (including intrathecal or intraventricular, administration).

Pharmaceutical compositions and formulations for topical administration include but are not limited to ointments, lotions, creams, transdermal patches, gels, drops, suppositories, sprays, liquids and powders. Utilization of conventional pharmaceutical carriers, oily bases, aqueous, powder, thickeners and the like may be used in the formulations.

The pharmaceutical compositions may also be administered in tablets, capsules, gel capsules, and the like.

Penetration enhancers may also be used in the instant pharmaceutical compositions. Such enhancers include surfactants, fatty acids, bile salts, chelating agents, and non-chelating non-surfactants. Such enhancers are generally described in U.S. Pat. No. 6,287,860, which is incorporated herein by reference.

In addition to treatment of diseases or other conditions, compositions disclosed herein may also be useful prophylactically.

In some preferred embodiments, the hydrogels can be delivered locally either via implantation or as an injection procedure, potentially through syringes or catheters.

Due to the variety of therapeutic agents that can be utilized with the cross-linked hydrogel systems, a wide variety of diseases and disorders can be treated with the technology described herein. Post MI remodeling is one application of the proposed therapeutic approach. In addition, the disclosed concept could be applied in any ailment in which MMPs contribute to the pathophysiology of the disease. Treatment methods comprise administration of the instant compositions by any appropriate method to a patient in need of such treatment. In some embodiments, the patent is a mammal. In certain preferred embodiments, the patient is a human.

The invention is illustrated by the following examples which are intended to be illustrative and not limiting in scope.

EXAMPLES

Unless noted otherwise, all percentages are by weight.

Example 1

Synthesis of HA-Aldehyde

Figure 1:
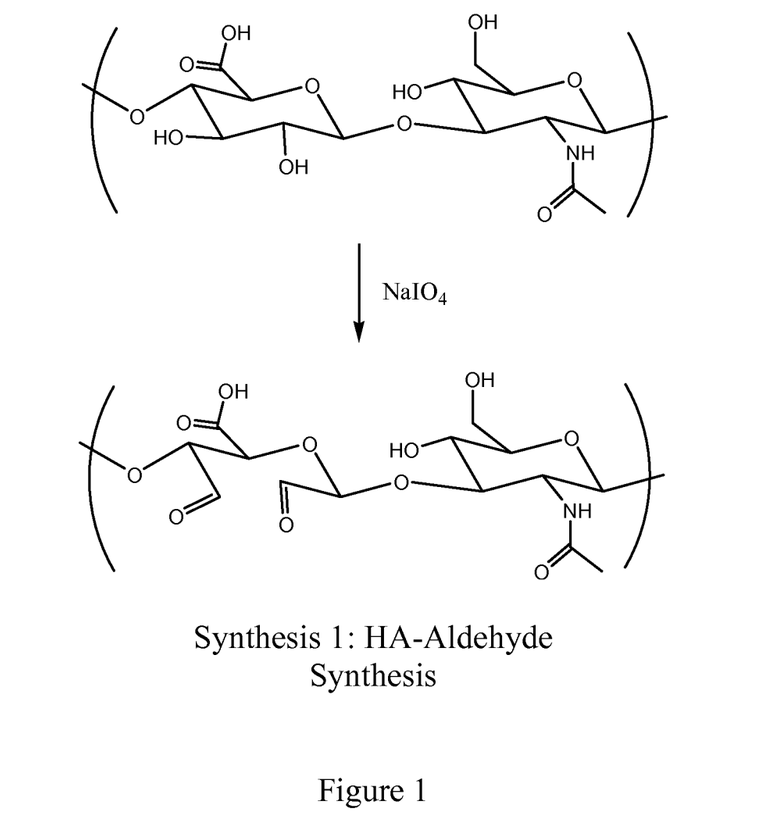
FIG. 1 illustrates synthesis of HA-aldehyde (Synthesis 1) for use in forming a hydrogel.
Figure 2:
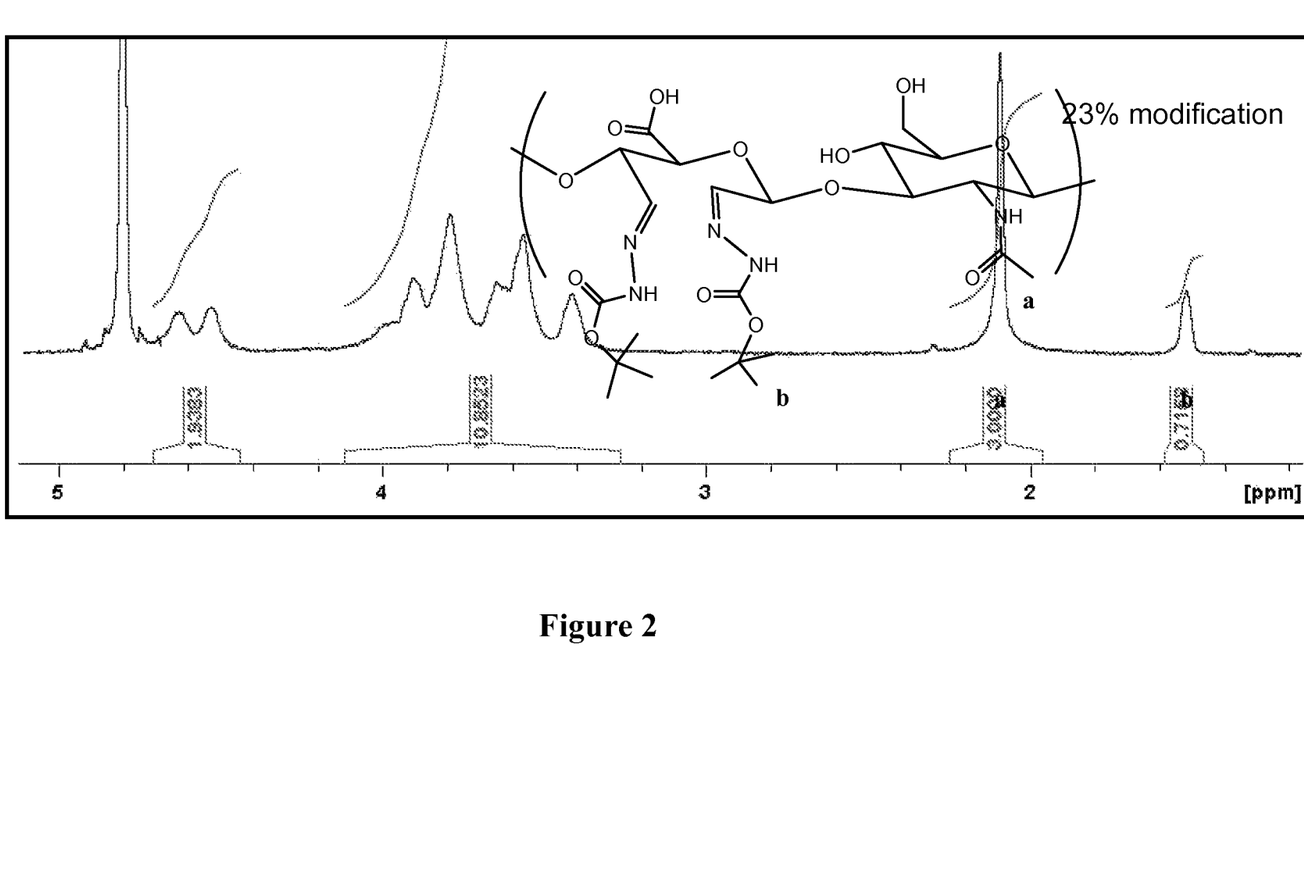
FIG. 2 presents analytical analysis of the HA-aldehyde shown in FIG. 1.

Hyaluronic acid (HA) is contacted with $NaIO_4$ to produce the aldehyde derivative (Synthesis 1) depicted in FIG. 1. FIG. 2 presents analytical data for the HA-aldehyde.

Example 2

Synthesis of HA-peptide Hydrazide

Figure 3:
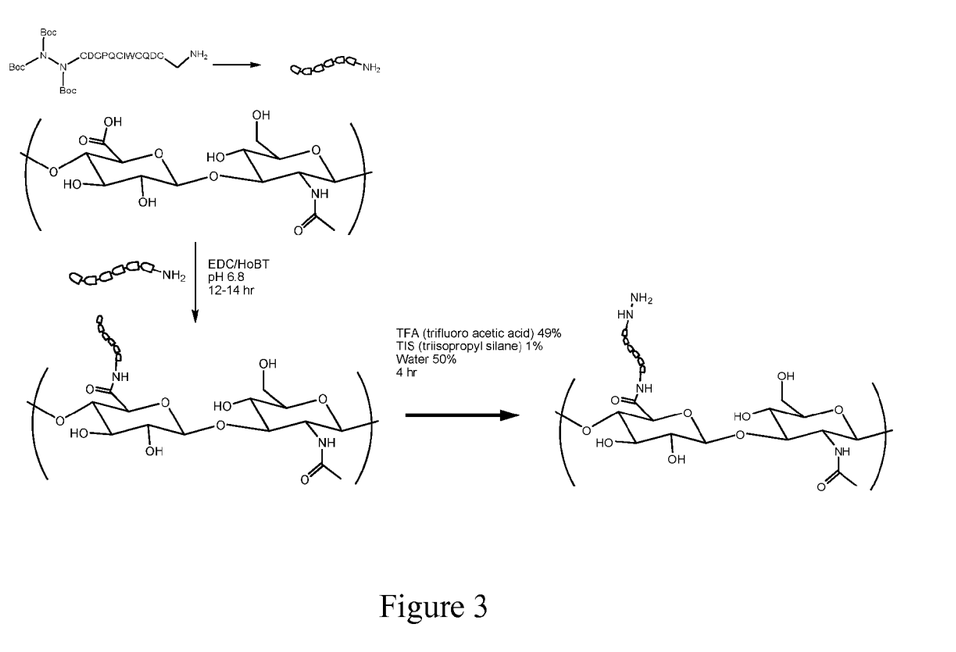
FIG. 3 illustrates synthesis of HA-peptide hydrazide for use in forming the hydrogel. The product has a hyaluronic acid backbone modified with either an aldehyde or a peptide with a hydrazide end.

Hyaluronic acid (HA) is contacted with EDC/HoBT at ph 6.8 for 12-14 hours to produce the intermediate depicted in FIG. 3. The intermediate is then contacted with trifluoroacetic acid (TFA, 49%), trisopropyl silane (TIS, 1%), and water (50%) for 4 hours to produce the hydrazide depicted in FIG. 3. EDC is ethyl-(N',N'-dimethylamino) propylcarbodiimide hydrochloride (EDC). HoBT is 1-hydroxybenzotriazole. One peptide that could be used is GCRDGPQGI-WGQDRCG, which cleaves in the presence of MMP-2, but somewhat nonspecifically. In the example, the cross-linker utilized was of the formula:

the peptide being of the sequence GDGPQGIWGQDG.

Example 3

HA-Hydrazide Synthesis

Figure 4:
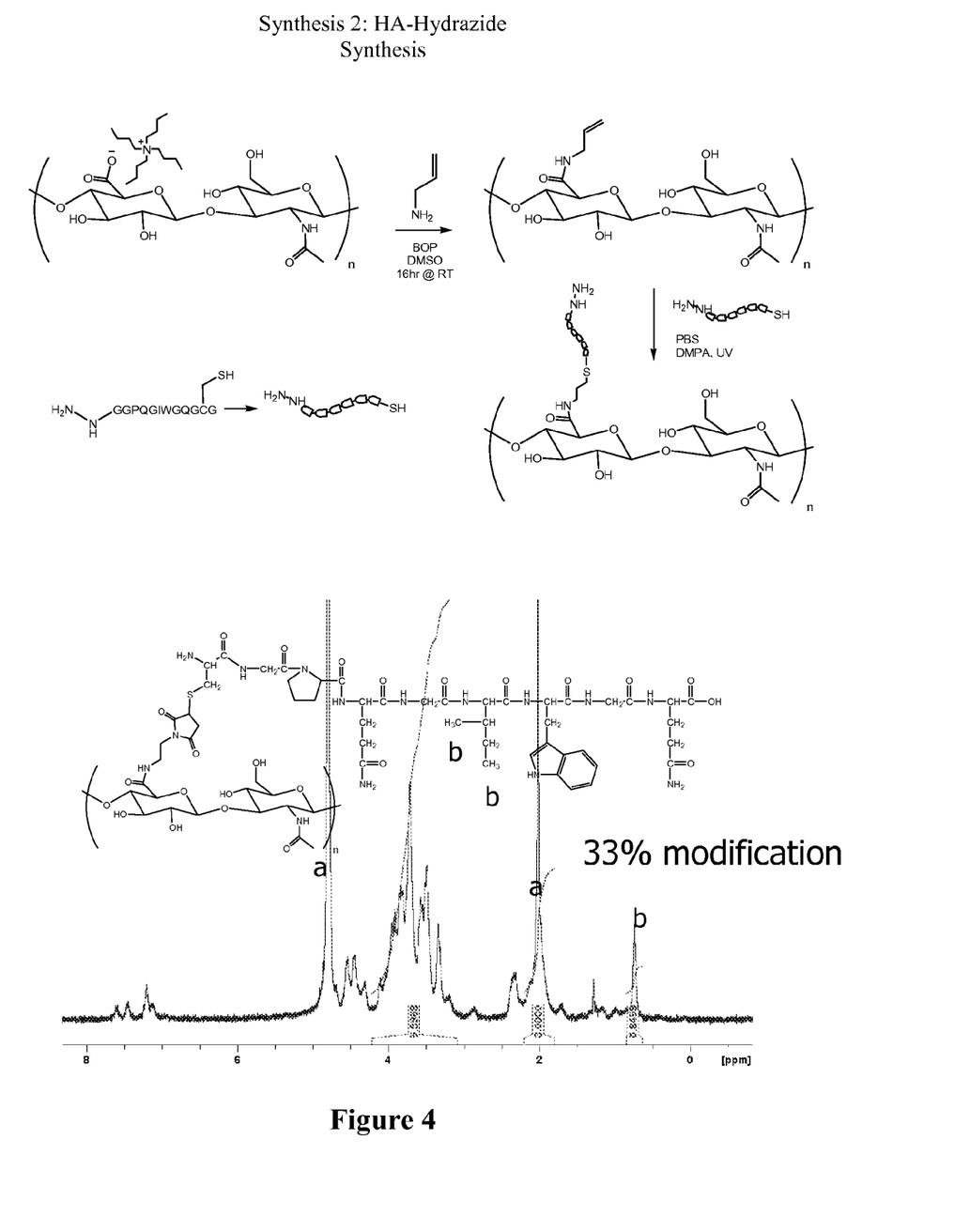
FIG. 4 illustrates synthesis of HA-hydrazide (Synthesis 2). The example depicted in the figure has 33% modification.

HA-hydrazide synthesis (Synthesis 2) having 33% modification was performed as depicted in FIG. 4. The peptide utilized was of the formula:

which is represented by the shorthand in the figure which shows the —SH, —NH— and —NH$_2$ groups with the string of amino acids represented by the string of 6 rectangular structures.

Analytical analysis of the product is also presented in FIG. 4.

Example 4

Hydrogel Formation

Figure 5:
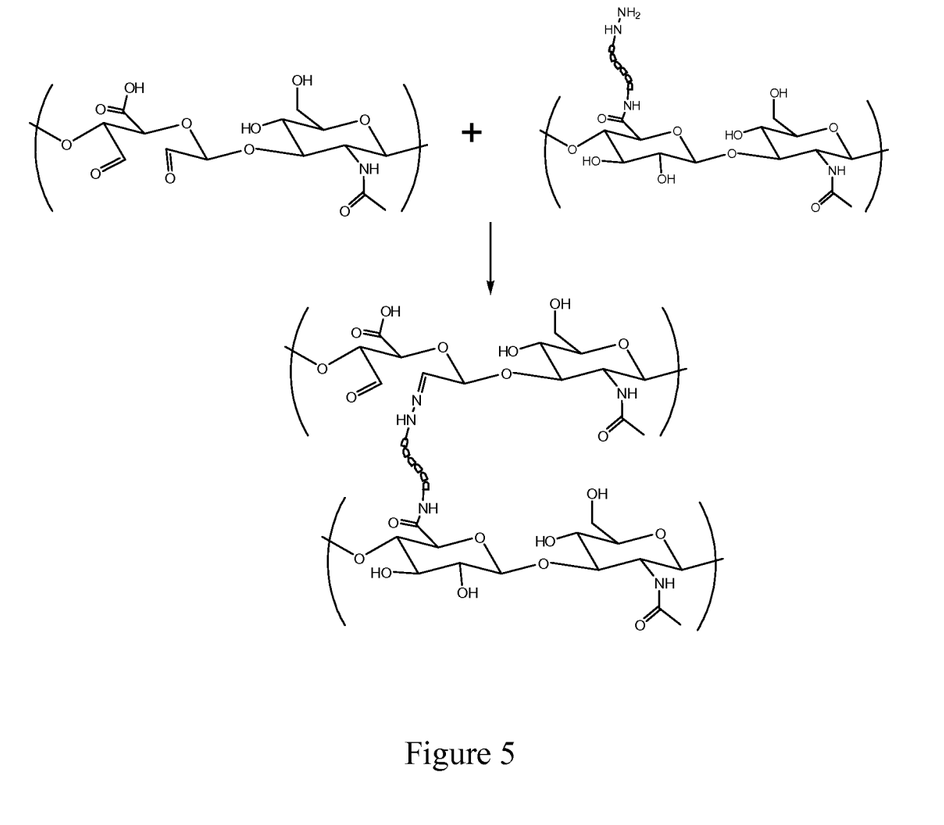
FIG. 5 illustrates formation of a hydrogel by mixing precursors containing a hyaluronic acid backbone modified with either an aldehyde or a peptide with a hydrazide end. By using a peptide that is MMP sensitive, the gel will form an enzyme sensitive hydrogel.

Hydrogel formed by mixing the aldehyde of Example 1 with the hydrazide of Example 2 to form the hydrogel depicted in FIG. 5.

Example 5

Gel Formation Through Mixing of Synthesis 1 and Synthesis 2

Figure 6:
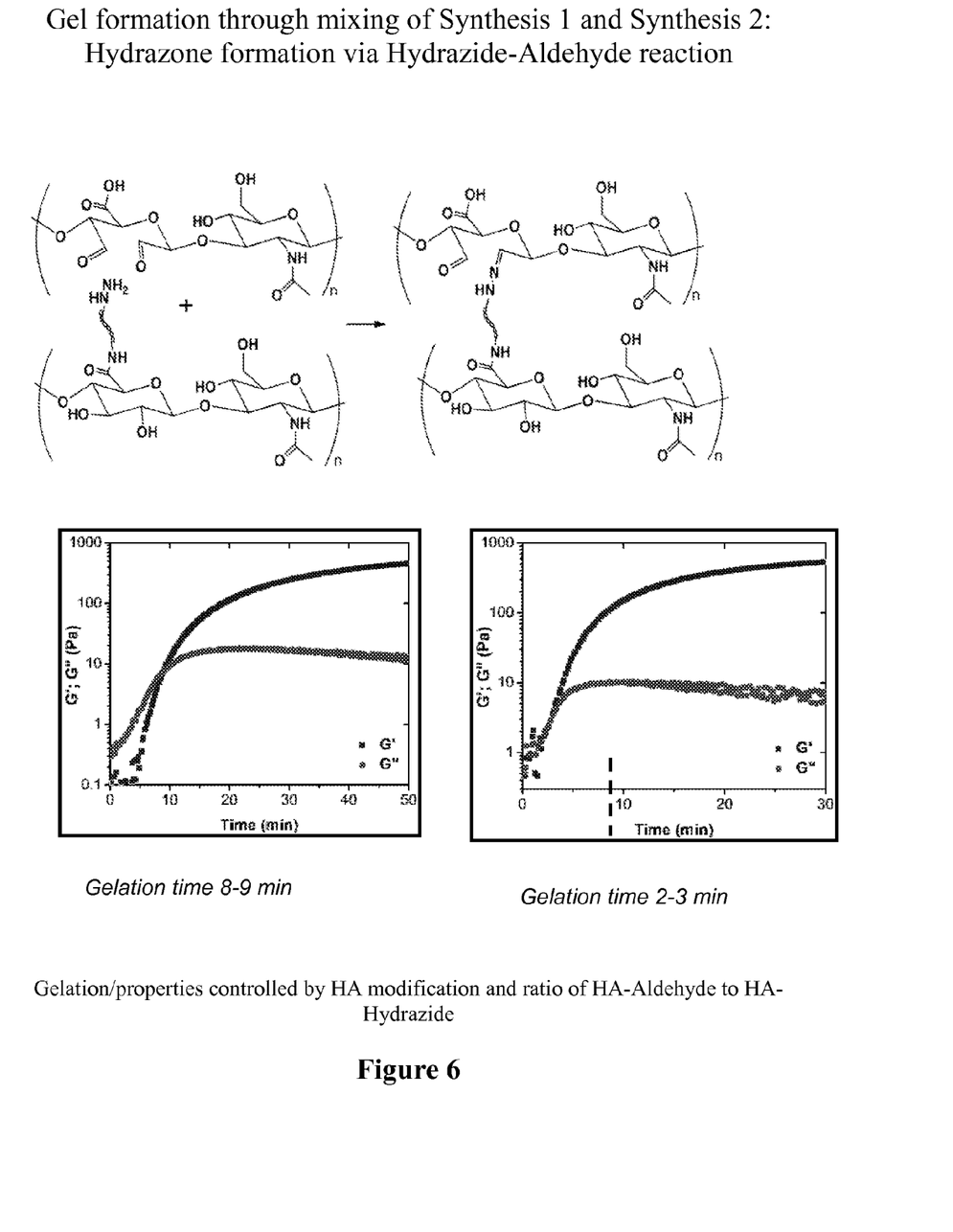
FIG. 6 illustrates gel formation through mixing of Synthesis 1 and Synthesis 2: hydrazone formation via hydrazide-aldehyde reaction. Gelation/properties can be controlled by HA modification and ratio of HA-aldehyde to HA-hydrazide.

Gel was formed through a mixing of the products of synthesis 1 and synthesis 2 as presented in FIG. 6. Gelation/properties can be controlled by HA modification and ratio of HA-aldehyde to HA-hydrazide. Differences in time are illustrated by the plots presented in FIG. 6.

Example 6

MMP-Specific Gel Synthesis

Figure 7:
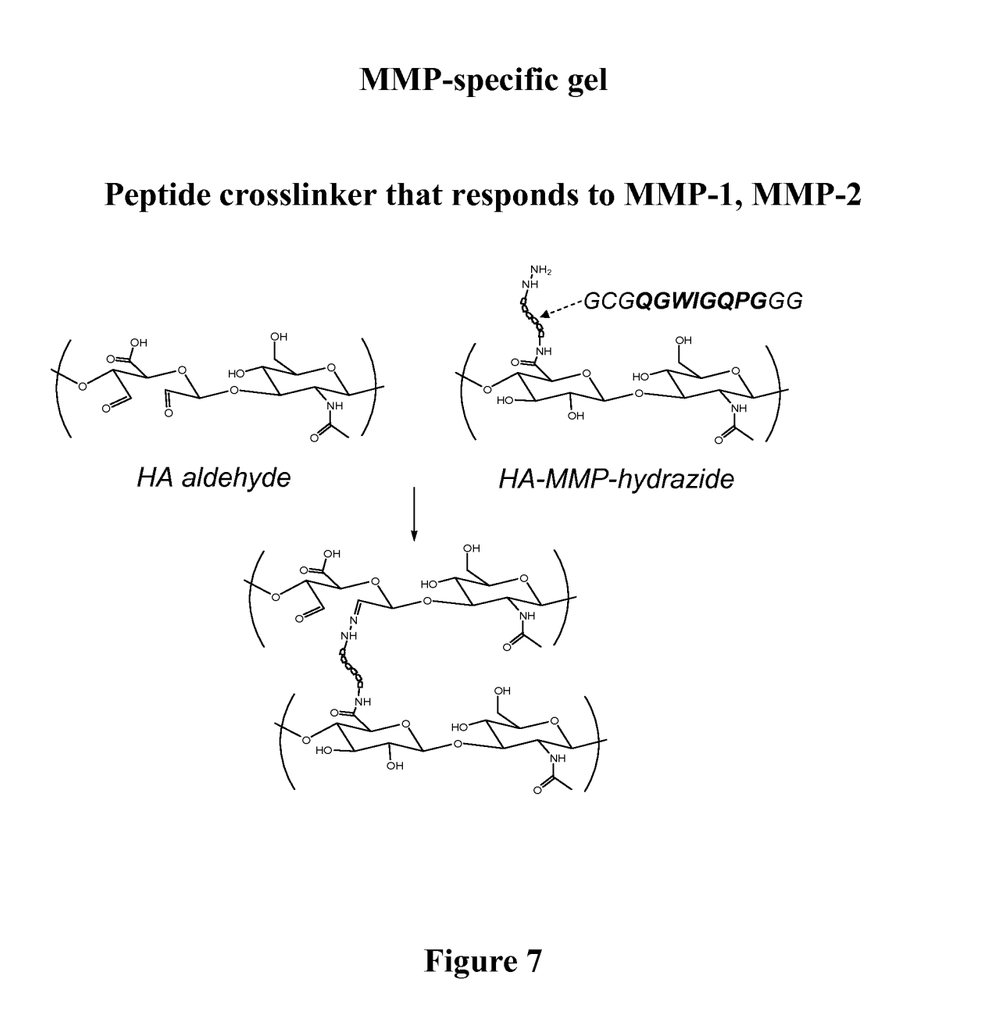
FIG. 7 illustrates a MMP-specific gel with a peptide crosslinker that responds to MMP-1, MMP-2.
Figure 8:
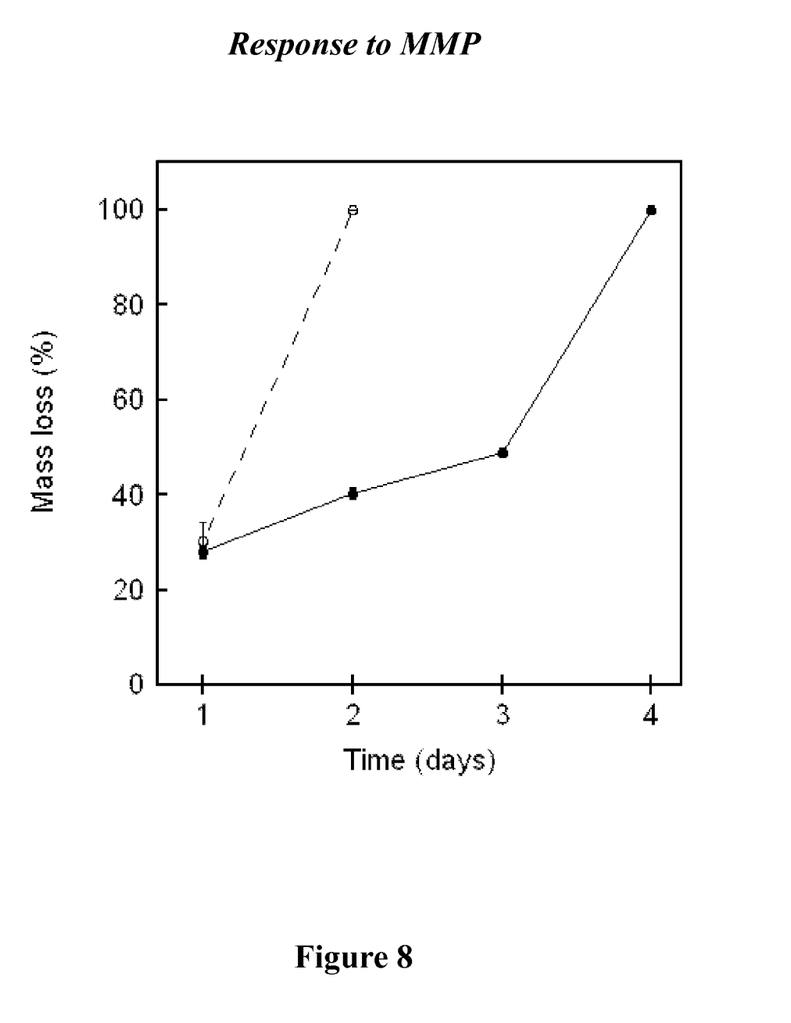
FIG. 8 illustrates mass loss with the gel of FIG. 7 as a function of time upon exposure to MMP (at day 1 or day 3).

FIG. 7 shows a MMP-specific gel with a peptide cross-linker that responds to MMP-1, MMP-2. In this example, the peptide has the sequence GCGQGWIGQPGGG. Response to MMP of this gel is illustrated in FIG. 8.

Example 7

Crosslinking of an Acrylated Hyaluronic Acid

Figure 9:
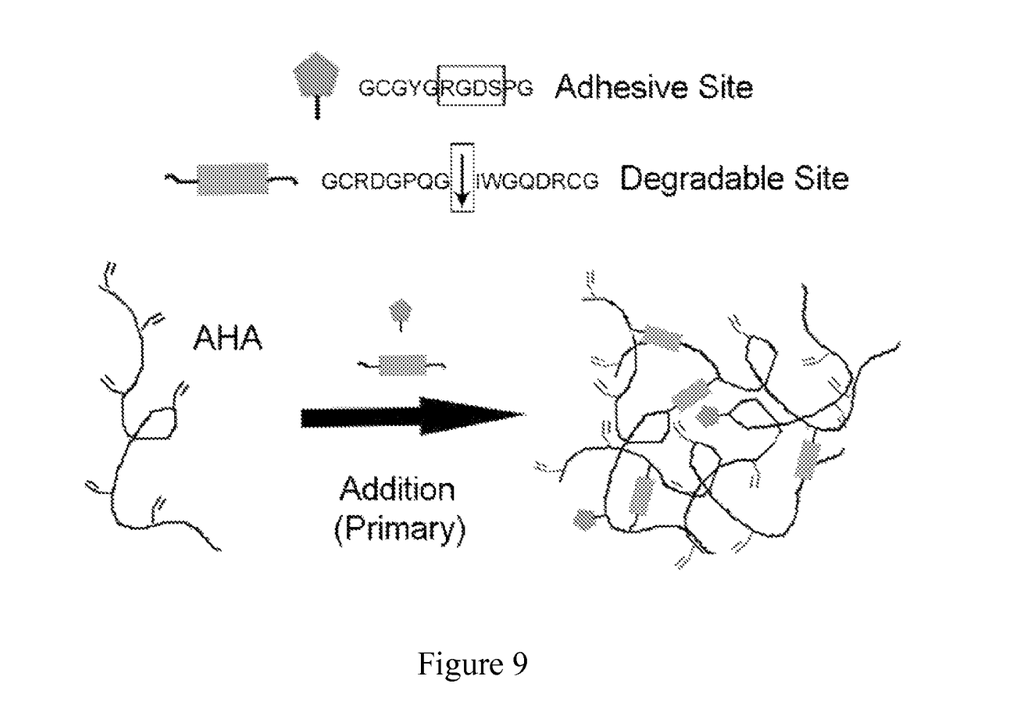
FIG. 9 illustrates the crosslinking of an acrylated hyaluronic acid with a peptide (containing thiols on each end).

Schematic of the crosslinking of an acrylated hyaluronic acid with a peptide (containing thiols on each end) if depicted in FIG. 9.

---

What is claimed:

1. A process for delivery of an inhibitor of matrix metalloprotease to the extracellular matrix of targeted tissue comprising:
 administering a hydrogel composition to a patient; said hydrogel composition comprising:
 biocompatible hydrogel, said hydrogel comprising a plurality of cross-linkers connecting backbone components of said hydrogel; and
 a therapeutic agent comprising an inhibitor of matrix metalloprotease encapsulated within said hydrogel;
 wherein said hydrogel is cross-linked utilizing a cross-linker comprising a peptide sequence that is capable of being degraded by a matrix metalloprotease; said inhibitor being effective as a treatment of a condition related to the presence of said matrix metalloprotease;
 wherein said hydrogel contains binding groups to said inhibitor of matrix metalloprotease to retain the inhibitor within the intact hydrogel;
 allowing said hydrogel composition to contact matrix metalloprotease in said extracellular matrix of targeted tissue;
 said contact resulting in the release of at least a portion of said inhibitor of matrix metalloprotease.

2. The process of claim 1, wherein said tissue inhibitor of matrix metalloprotease is TIMP-3.

3. The process of claim 1, wherein said matrix metalloprotease is MMP-13 or MMP-2.

4. The process of claim 1, wherein the delivery is accomplished through a syringe or catheter.

5. The process of claim 1, wherein the delivery is accomplished by intravenous, intraarterial, subcutaneous, intraperitoneal or intramuscular injection.

6. The process of claim 1, wherein said hydrogel comprises hyaluronic acid.

7. The process of claim 1, wherein the hydrogel composition is such that encapsulated inhibitors are released from the hydrogel and into the extracellular matrix of tissue in the presence of pathological levels of matrix metalloprotease.

8. The process of claim 1, wherein said peptide comprising a sequence GCRDGPQGIWGQDRCG, GGPQGIWGQGCG, or GCGQGWIGQPGGG.

9. The process of claim 1, wherein said peptide sequence is incorporated into the cross-linker via reaction of thiol groups of cysteins with acrylates or methacrylates.

10. The process of claim 1, wherein the patient is a mammal.

11. The process of claim 1, wherein the patient is a human.

12. The process of claim 1, wherein the delivery is accomplished through a syringe.

13. The process of claim 1, wherein the delivery is accomplished through a catheter.

14. The process of claim 1, wherein the patient is in need of treatment for myocardial infarction.

15. The process of claim 1, wherein inhibitor of matrix metalloprotease reduces left ventricular remodeling associated with myocardial infarction in said patient.

16. The process of claim 1, wherein said binding groups attenuate diffusion of encapsulated inhibitors from the hydrogel.

17. The process of claim 1, wherein said peptide cross-linker is degraded by a matrix metalloproteinase.

18. The process of claim 1, wherein said inhibitor diffuses from the hydrogel as the crosslinkers are degraded.

19. A process for delivery of an inhibitor of matrix metalloprotease to the extracellular matrix of targeted tissue comprising:
 administering a hydrogel composition to a patient; said hydrogel composition comprising:
 biocompatible hydrogel comprising hyaluronic acid, said hydrogel comprising a plurality of cross-linkers connecting backbone components of said hydrogel; and
 a therapeutic agent comprising an inhibitor of matrix metalloprotease encapsulated within said hydrogel;
 wherein said hydrogel is cross-linked utilizing a cross-linker comprising a peptide sequence that is capable of being degraded by a matrix metalloprotease; said inhibitor being effective as a treatment of a condition related to the presence of said matrix metalloprotease;
 wherein said hydrogel contains binding groups to said inhibitor of matrix metalloprotease to retain the inhibitor within the intact hydrogel;
 allowing said hydrogel composition to contact matrix metalloprotease in said extracellular matrix of targeted tissue;
 said contact resulting in the release of at least a portion of said inhibitor of matrix metalloprotease.

* * * * *

SEQUENCE LISTING

```
<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Gly Cys Arg Asp Gly Pro Gln Gly Ile Trp Gly Gln Asp Arg Cys Gly
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide

<400> SEQUENCE: 2

Gly Gly Pro Gln Gly Ile Trp Gly Gln Gly Cys Gly
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide

<400> SEQUENCE: 3

Gly Cys Gly Gln Gly Trp Ile Gly Gln Pro Gly Gly Gly
1               5                   10

<210> SEQ ID NO 4
```

```
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

Gly Asp Gly Pro Gln Gly Ile Trp Gly Gln Asp Gly
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Gly Cys Gly Tyr Gly Arg Gly Asp Ser Pro Gly
1               5                   10
```

UNITED STATES PATENT AND TRADEMARK OFFICE
CERTIFICATE OF CORRECTION

PATENT NO. : 9,694,081 B2
APPLICATION NO. : 13/805501
DATED : July 4, 2017
INVENTOR(S) : Jason Alan Burdick et al.

It is certified that error appears in the above-identified patent and that said Letters Patent is hereby corrected as shown below:

In the Specification

Column 1,
Lines 15-18, delete "This invention was made with government support under Contract No. Grant/Contract Number R01 HL111090 awarded by the National Institutes of Health (NIH). The Government has certain rights in the herein disclosed subject matter." and insert -- This invention was made with government support under grant number HL063954 and HL111090 awarded by the National Institutes of Health. The government has certain rights in the invention. --

Signed and Sealed this
Thirtieth Day of July, 2019

Andrei Iancu
*Director of the United States Patent and Trademark Office*